US00PP35938P3

(12) United States Plant Patent
Flore

(10) Patent No.: US PP35,938 P3
(45) Date of Patent: Jul. 2, 2024

(54) ***PHALAENOPSIS* PLANT NAMED 'MI02145'**

(50) Latin Name: *Phalaenopsis hybrida*
Varietal Denomination: MI02145

(71) Applicant: MICROFLOR N.V., Lochristi (BE)

(72) Inventor: Febe Flore, Lochristi (BE)

(73) Assignee: MICROFLOR N.V., Lochristi (BE)

( * ) Notice: Subject to any disclaimer, the term of this patent is extended or adjusted under 35 U.S.C. 154(b) by 0 days.

(21) Appl. No.: 18/214,312

(22) Filed: Jun. 26, 2023

(65) Prior Publication Data

US 2023/0422647 P1 Dec. 28, 2023

Related U.S. Application Data

(60) Provisional application No. 63/356,011, filed on Jun. 27, 2022.

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
See application file for complete search history.

*Primary Examiner* — Susan McCormick Ewoldt
*Assistant Examiner* — Zachariah Allan Kay
(74) *Attorney, Agent, or Firm* — C. Anne Whealy

(57) ABSTRACT

A new and distinct cultivar of *Phalaenopsis* plant named 'MI02145', characterized by its upright plant habit; vigorous growth habit and rapid growth rate; strong and flexible flowering stems; relatively compact and arching leaves; freely flowering habit with typically about two inflorescences per plant, each inflorescence with numerous flowers; purple violet-colored flowers with darker purple violet-colored venation; and good postproduction longevity.

1 Drawing Sheet

Figure 1:
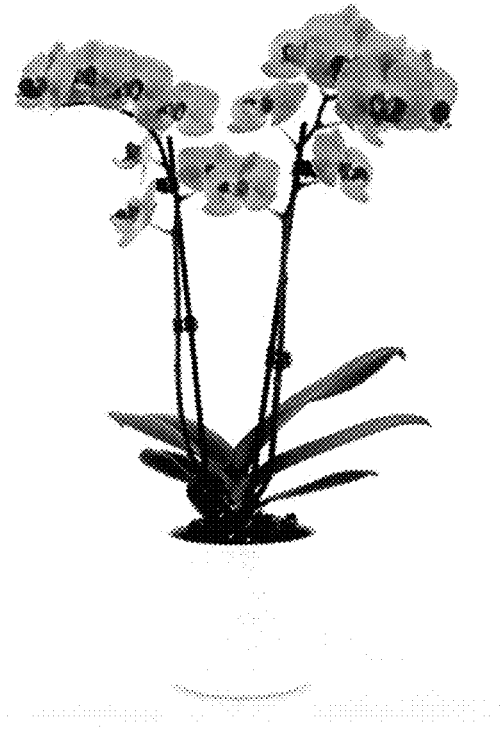

Botanical designation: *Phalaenopsis hybrida.*
Cultivar denomination: 'MI02145'.

A European Community Plant Breeder's Rights application for the instant plant was filed by the Applicant/Assignee of the instant application, Microflor N. V. of Lochristi, Belgium on Sep. 28, 2021, application number 2021/2390. Foreign priority is not claimed to this application.

BACKGROUND OF THE INVENTION

The present invention relates to a new and distinct cultivar of *Phalaenopsis* plant, botanically known as *Phalaenopsis hybrida*, and hereinafter referred to by the name 'MI02145'.

The new *Phalaenopsis* plant is a product of a planned breeding program conducted by the Inventor in Lochristi, Belgium. The objective of the breeding program is to develop new freely flowering *Phalaenopsis* plants with good leaf shape and relatively large flowers with unique and attractive flower coloration.

The new *Phalaenopsis* plant originated from a cross-pollination by the Inventor in October, 2015 in Lochristi, Belgium of a proprietary selection of *Phalaenopsis hybrida* identified as code number PHM00567, not patented, as the female, or seed, parent with a proprietary selection of *Phalaenopsis hybrida* identified as code number PHM00564, not patented, as the male, or pollen, parent. The new *Phalaenopsis* plant was discovered and selected by the Inventor as a single flowering plant from within the progeny of the stated cross-pollination grown in a controlled greenhouse environment in Lochristi, Belgium in May, 2018.

Asexual reproduction of the new *Phalaenopsis* plant by in vitro meristem propagation in a controlled environment in Lochristi, Belgium since December, 2019 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'MI02145'. These characteristics in combination distinguish 'MI02145' as a new and distinct *Phalaenopsis* plant:

1. Upright plant habit.
2. Vigorous growth habit and rapid growth rate.
3. Strong and flexible flowering stems.
4. Relatively compact and arching leaves.
5. Freely flowering habit with typically about two inflorescences per plant, each inflorescence with numerous flowers.
6. Purple violet-colored flowers with darker purple violet-colored venation.
7. Good postproduction longevity.

Plants of the new *Phalaenopsis* can be compared to plants of the female parent selection. Plants of the new *Phalaenopsis* differ primarily from plants of the female parent selection in the following characteristics:

1. Plants of the new *Phalaenopsis* have smaller flowers than plants of the female parent selection.
2. Flowers of plants of the new *Phalaenopsis* are purple violet in color whereas flowers of plants of the female parent selection are light purple in color.

3. Flowers of plants of the new *Phalaenopsis* do not have cirrhose tips whereas flowers of plants of the female parent selection have cirrhose tips.

Plants of the new *Phalaenopsis* can be compared to plants of the male parent selection. Plants of the new *Phalaenopsis* differ primarily from plants of the male parent selection in the following characteristics:

1. Plants of the new *Phalaenopsis* have smaller flowers than plants of the male parent selection.
2. Flowers of plants of the new *Phalaenopsis* are darker purple violet in color than flowers of plants of the male parent selection.
3. Flowers of plants of the new *Phalaenopsis* do not have cirrhose tips whereas flowers of plants of the male parent selection have cirrhose tips.

Plants of the new *Phalaenopsis* can be compared to plants of *Phalaenopsis hybrida* 'PHALFOTJ', disclosed in U.S. Plant Pat. No. 31,948. In side-by-side comparisons, plants of the new *Phalaenopsis* differ primarily from plants of 'PHALFOTJ' in the following characteristics:

1. Flowers of plants of the new *Phalaenopsis* are smaller than flowers of plants of 'PHALFOTJ'.
2. Flowers of plants of the new *Phalaenopsis* are purple violet in color whereas flowers of plants of 'PHALFOTj' are reddish purple in color.
3. Flowers of plants of the new *Phalaenopsis* do not have cirrhose tips whereas flowers of plants of 'PHALFOTJ' have cirrhose tips.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph at the top of the sheet (FIG. 1) is a side perspective view of a typical flowering plant of 'MI02145' grown in a container.

Figure 2:
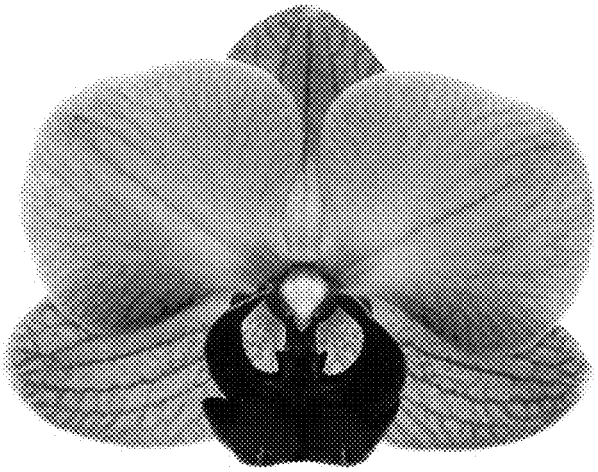

The photograph at the bottom of the sheet (FIG. 2) is a close-up view of a typical flower of 'MI02145'.

DETAILED BOTANICAL DESCRIPTION

The aforementioned photographs and following observations and measurements describe plants grown during the winter in 12-cm containers in a glass-covered greenhouse in Lochristi, Belgium and under cultural practices typically used in commercial *Phalaenopsis* production. During the production of the plants, day and night temperatures ranged from 18C to 29C and light levels ranged from 150 Watt/$m^2$ to 375 Watt/$m^2$. Plants were 74 weeks old when the photographs were taken and 71 weeks old when the description was taken. In the following description, color references are made to The Royal Horticultural Society Colour Chart, 2001 Edition, except where general terms of ordinary dictionary significance are used.

Botanical classification: *Phalaenopsis hybrida* 'MI02145'.

Parentage:

*Female parent*.—Proprietary selection of *Phalaenopsis hybrida* identified as code number PHM00567, not patented.

*Male parent*.—Proprietary selection of *Phalaenopsis hybrida* identified as code number PHM00564, not patented.

Propagation:

*Type*.—By in vitro meristem propagation.

*Time to initiate roots, summer*.—About nine to ten weeks at temperatures about 26C.

*Time to initiate roots, winter*.—About ten to eleven weeks at temperatures about 26C.

*Time to produce a rooted young plant, summer*.—About 140 to 160 days at temperatures about 26C.

*Time to produce a rooted young plant, winter*.—About 150 to 180 days at temperatures about 26C.

*Root description*.—Thick, fleshy; typically grey green in color; actual color of the roots is dependent on substrate composition, water quality, fertilizer, substrate temperature and age of roots.

*Rooting habit*.—Small amount of branching; sparse.

Plant description:

*Plant form in and growth habit*.—Herbaceous epiphyte; upright plant habit with typically two inflorescences per plant, each inflorescence with numerous flowers; monopodial; vigorous growth habit and rapid growth rate.

*Plant height, substrate level to top of foliar plane*.—About 12 cm.

*Plant height, substrate level to top of inflorescences*.—About 38 cm.

*Plant diameter or spread*.—About 28 cm.

Leaf description:

*Arrangement and quantity*.—Distichous, simple; sessile; about seven leaves per plant; relatively compact.

*Length*.—About 15 cm.

*Width*.—About 7 cm.

*Aspect*.—Outwardly arching.

*Shape*.—Elliptic to slightly oblanceolate.

*Apex*.—Unequal obtuse; occasionally slightly and unequally retuse.

*Base*.—Sheathing.

*Margin*.—Entire.

*Texture and luster, upper and lower surfaces*.—Smooth, glabrous; moderately glossy.

*Venation pattern*.—Camptodromous.

*Color*.—When opening, upper surface: Close to 137A. When opening, lower surface: Close to 137C. Fully expanded leaves, upper surface: Close to between 137A and 139A; venation, close to between 137A and 139A. Fully expanded leaves, lower surface: Close to 137C; venation, close to 137C.

Inflorescence description:

*Appearance and flowering habit*.—Showy zygomorphic flowers arranged on axillary branched racemes; typically two inflorescences per plant and ranging from one to three; each inflorescence with about 13 flowers; flowers face outwardly on arching inflorescences supported by upright peduncles; flowers with three petals, two lateral petals and one center petal transformed into a labellum and three sepals.

*Fragrance*.—None detected.

*Time to flower*.—Plants begin flowering about 17 weeks after an inductive cooling period; flowers open about five weeks after flower buds develop.

*Flower longevity*.—Long flowering period, individual flowers maintain good substance for about nine weeks on the plant; flowers not persistent.

*Inflorescence length* (*lowermost flower to inflorescence apex*).—About 17 cm.

*Inflorescence width*.—About 17 cm.

*Flower buds*.—Height: About 1.8 cm. Diameter: About 1.5 cm. Shape: Ovate. Color: Close to 148D; towards the edges, close to 87C.

*Flower diameter*.—About 5.4 cm.

*Flower depth*.—About 4.5 cm.

*Petals, quantity and arrangement*.—Three, two lateral petals and one center petal transformed into a labellum.

*Lateral petals*.—Length: About 2.6 cm. Width: About 2.9 cm. Shape: Orbicular to deltoid. Apex: Rounded. Margin: Entire. Texture and luster, upper and lower surfaces: Smooth, glabrous, velvety; matte. Color: When opening and fully opened, upper surface: Close to 82B; venation, close to 87A; color does not change with subsequent development. When opening and fully opened, lower surface: Close to 76B; venation, close to 76B; color does not change with subsequent development.

*Labella*.—Appearance: Tri-lobed with two lateral lobes and a central lobe. Length: About 2.1 cm. Width: About 3.3 cm. Shape, lateral and central lobes: Deltoid; fused into a tubular shape. Apex, lateral and central lobes: Emarginate. Margins, lateral and central lobes: Entire. Texture and luster, upper and lower surfaces: Smooth, glabrous, moderately velvety; matte. Callosities: Located at the base of the labellum and attachment point of the lateral petals; about 3 mm in length, about 4 mm in width and about 4 mm in height. Color: When opening and fully opened, upper surface: Lateral and central lobes: Distally, close to 83B and proximally, close to 83A; stripes, close to 15A. Callosities: Close to 83B. When opening and fully opened, lower surface: Lateral and central lobes: Close to 76D; towards the margins, close to 83C.

*Sepals*.—Quantity and arrangement: Three, two lower lateral sepals and one upper dorsal sepal. Length, lateral sepal: About 2.6 cm. Width, lateral sepals: About 2.2 cm. Length, dorsal sepal: About 2.7 cm. Width, dorsal sepal: About 1.9 cm. Shape, lateral sepals: Lanceolate; asymmetrical. Shape, dorsal sepal: Elliptical. Apex, lateral sepals: Bluntly acute to obtuse. Apex, dorsal sepal: Obtuse. Base, lateral and dorsal sepals: Acute to obtuse. Margin, lateral and dorsal sepals: Entire. Texture and luster, lateral and dorsal sepals, upper and lower surfaces: Smooth, glabrous, velvety; matte. Color, lateral and dorsal sepals: When opening, upper surface: Close to 82C; venation, close to 82B. When opening, lower surface: Close to 148D; towards the margins, close to 87C. Fully opened, upper surface: Close to 82C; venation, close to 82B. Fully opened, lower surface: Close to 76D; towards the margins, close to 76C.

*Peduncles*.—Length: About 38 cm. Diameter: About 5 mm. Strength: Strong, somewhat flexible. Aspect: Mostly upright. Texture and luster: Smooth, glabrous; matte. Color: Close to 200A; fine lines and dots, close to 148A.

*Pedicels*.—Length: About 2.4 cm. Diameter: About 3 mm. Strength: Moderately strong. Aspect: About 90 degrees from peduncle axis. Texture and luster: Smooth, glabrous; matte. Color: Proximally, close to 148B and distally, close to 76D.

*Reproductive organs*.—Androecium: Column length: About 8 mm. Column width: About 5 mm. Column color: Close to 82A. Pollinia quantity: Two. Pollinia diameter (per two pollinia): About 2 mm. Pollinia color: Close to 25A. Gynoecium: Stigma length: About 2 mm. Stigma width: About 4 mm. Stigma shape: Reniform. Stigma color: Close to 76C. Ovary length: About 6 mm. Ovary diameter: About 2 mm. Ovary color: Close to 76D. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate temperatures ranging from about 10C to about 40C.

It is claimed:

1. A new and distinct *Phalaenopsis* plant named 'MI02145' as illustrated and described herein.

* * * * *